US006498150B2

(12) United States Patent
Taub et al.

(10) Patent No.: US 6,498,150 B2
(45) Date of Patent: *Dec. 24, 2002

(54) LOW MOLECULAR WEIGHT CELL, BONE MARROW AND IMMUNE STIMULANTS

(75) Inventors: Floyd Taub, Silver Spring, MD (US); Thomas J. Perun, Round Lake, IL (US); Christopher K. Murray, Longmont, CO (US); Randall J. Daughenbaugh, Longmont, CO (US); Daniel Lednicer, Rockville, MD (US)

(73) Assignee: Dovetail Technologies, Inc., College Park, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/414,071

(22) Filed: Oct. 7, 1999

(65) Prior Publication Data

US 2002/0035118 A1 Mar. 21, 2002

Related U.S. Application Data

(63) Continuation of application No. 08/733,174, filed on Oct. 17, 1996, now Pat. No. 6,007,819.
(60) Provisional application No. 60/005,336, filed on Oct. 17, 1995.

(51) Int. Cl.[7] ...................... A61K 31/275; C07F 9/02; C07C 239/00; C07C 309/00; C07C 259/00; C07C 381/50

(52) U.S. Cl. .................. 514/79; 546/22; 514/212; 514/277; 514/408; 514/89; 514/528; 514/91; 540/484; 548/400; 558/166; 558/170; 560/312; 562/102; 562/109; 564/123; 564/193; 568/63

(58) Field of Search .................. 514/212, 277, 514/408, 528; 540/484; 546/1; 548/400; 556/24; 558/170, 166; 560/312; 562/102, 109; 564/123, 193, 204; 568/63

(56) References Cited

U.S. PATENT DOCUMENTS 3,789,125 A  1/1974  Kuger et al.

(List continued on next page.)

FOREIGN PATENT DOCUMENTS

| AU | 655598 | 7/1991 |
| EP | 0 538 330 B1 | 10/1995 |
| WO | WO 97/14306 | 4/1997 |

OTHER PUBLICATIONS

Knight, G.D. et al. Seemingly Diverse Activities of B-Alethine. Cancer Research. Nov. 1, 1994. vol. 54, pp. 5636–5642. see especially Abstract. Figure 1 and p. 5636–5637.

*Primary Examiner*—Alan L. Rotman
*Assistant Examiner*—Taylor V. Oh
(74) *Attorney, Agent, or Firm*—Judith A. Evans; Paul D. Roath (57) ABSTRACT

The present invention relates to peptide-like compounds, eg aminocarboxylic acid amide derivatives, and to methods of using same to stimulate cells of the immune system, bone marrow and other organs. The present compounds can be used to enhance vaccination, increase synthesis of and enhance function of blood cell components and enhance anti-neoplastic effects of various agents. The compounds of the invention can be used to produce a variety of further pharmacologic effects.

5 Claims, 4 Drawing Sheets

U.S. PATENT DOCUMENTS

| | | |
|---|---|---|
| 4,102,948 A | 7/1978 | Feuer et al. |
| 4,218,404 A | 8/1980 | Feuer et al. |
| 5,085,860 A * | 2/1992 | Junino et al. .................. 424/72 |
| 5,578,313 A | 11/1996 | Knight et al. |
| 5,643,966 A | 7/1997 | Knight et al. |
| 6,007,819 A * | 12/1999 | Taub et al. ............... 424/184.1 |

* cited by examiner

Betathine ™ (β-alethine)

FIG.3B

Taurox SB (V₃)

FIG.3C

Taurox S (V₄)

FIG.3D

Taurox BOS

FIG.3E

Taurox OS

FIG.3F

Taurox BP

FIG.3G

Taurox P

FIG.3H

Taurox BOP

FIG.3I

Taurox OP

LOW MOLECULAR WEIGHT CELL, BONE MARROW AND IMMUNE STIMULANTS

This application is a continuation of Ser. No. 08/733,174 filed Oct. 17, 1996 now U.S. Pat. No. 6,007,819 which claims benefit of Ser. No. 60/005,336 filed Oct. 17, 1995.

TECHNICAL FIELD

The present invention relates to peptide-like compounds, eg aminocarboxylic acid amide derivatives, and to methods of using same to stimulate cells of the immune system, bone marrow and other organs. The present compounds can be used to enhance vaccination, increase synthesis of and enhance function of blood cell components and enhance anti-neoplastic effects of various agents. The compounds of the invention can be used to produce a variety of further pharmacologic effects.

BACKGROUND

A variety of polypeptide cytokines, hormones and immune system modulators have been used to stimulate production and activity of bone marrow-derived cells. However, little progress has been made in obtaining the same physiologic activities in culture and in vivo using simple, chemically synthesized small molecules. For example, there are relatively few reports of the use of simple, small molecules in stimulating production and function of various blood components, including, without limitation, red blood cells (RBCs) and white blood cells (WBCs), in stimulating the response to vaccinations, in enhancing differentiation and in the nontoxic treatment of neoplasia. The present invention relates to such methods, as well as others, and to compounds suitable for use in same.

OBJECTS AND SUMMARY OF THE INVENTION

It is an object of the present invention to provide compounds that exert an immunomodulatory effect. It is another object of the invention to provide a method of altering (eg stimulating) cellular productivity and vitality and to provide a method of modulating cell growth.

It is a specific object of the invention to provide a method of modulating immune function, for example, to facilitate vaccination against or treatment of diseases, including infectious and autoimmune diseases, as well as other diseases in which the immune system plays a role.

It is another specific object of the invention to provide a method of effecting blood cell stimulation (including RBCs, WBCs, stem cells, platelets and others).

It is a further specific object of the invention to provide a method of enhancing cell differentiation and cell growth and a method of exerting an anti-senescence effect in vitro and in vivo. It is also a specific object of the invention to provide a method of preserving viability of neurons, natural killer (NK) cells, fibroblasts and other cell types in vivo and in vitro. It is a further specific object of the invention to provide a method of exerting anti-Alzheimer and anti-aging effects and a method of treating genetic diseases related to aging. It is a further object of the invention to provide a method of enhancing bioactivity of cosmetics and compounds to serve as cosmeceuticals.

It is also a specific object of the invention to provide a method of treating a neoplastic or preneoplastic condition. It is another object of the invention to provide a method of an ameliorating side effects of various anti-neoplastic agents.

It is a further specific object of the invention to provide a method of altering (eg stimulating) cellular protein production, including antibody production.

The foregoing objects are met by the present invention which provides aminocarboxylic acid amide derivatives that can be used to produce a variety of biomodulatory effects, both in vivo and in vitro.

Further objects and advantages of the present invention will be clear from the description that follows.

DETAILED DESCRIPTION OF THE INVENTION

In a first embodiment, the present invention relates to compounds of the formula (I):

(I)

wherein:

A is a group of the formula $-PO_3H$, $-SO_3H$, $-OPO-(OH)_2$, $-OSO_2OH$, or $-SH$, or pharmaceutically acceptable salt thereof or physiologically hydrolyzable derivative thereof, or disulfide thereof when A is $-SH$. Suitable salts include sodium, potassium, calcium and zinc. Suitable hydrolyzable derivatizing groups include esters, such as substituted or unsubstituted lower alkyl (eg $C_1$ to $C_4$) or arylalkyl (eg benzyl) esters;

$R_1$ is H, a linear or branched lower alkyl, for example, a $C_1$ to $C_6$ alkyl, arylalkyl, for example, wherein the alkyl moiety is $C_1$ to $C_4$ alkyl and the aryl moiety is a substituted (eg lower alkyl or halogen) or unsubstituted phenyl group, or alkenyl (for example, $C_2$–$C_6$ alkenyl);

$R_2$ is H, a linear or branched lower alkyl, for example, a $C_1$ to $C_6$ alkyl, an alkenyl, for example, a $C_2$–$C_6$ alkenyl, an arylalkyl, for example, wherein the alkyl moiety is a $C_1$ to $C_4$ alkyl and the aryl moiety is a substituted (eg lower alkyl or halogen) or unsubstituted phenyl group; or an acyl, for example, acetyl, benzoyl, arylsulfonyl (for example, when the aryl moiety is phenyl); a carbonate ester such as alkoxycarbonyl (eg, $C_1$–$C_7$ alkoxy carbonyl) (for example, $-OCOC(CH_3)_3$); allyloxy carbonyl (eg $-OCOCH_2CH=CH_2$); cycloalkoxycarbonyl (eg when the ring is $C_3$–$C_8$ ($C_5$–$C_6$ being preferred) and when the alkoxy moiety is $C_1$–$C_8$) (for example $-OCOCH_2C_6H_5$); or an unsubstituted arylalkoxycarbonyl (for example $-OCOCH_2C_6H_5$) or a substituted arylalkoxycarbonyl wherein the substituent is, for example, a halogen, a nitro group, an amino group or a methoxyl group;

alternatively, $R^1$ and $R^2$ taken together form, with the nitrogen to which they are attached, a 5 to 7 membered ring (for example, $R^1$ and $R^2$ taken together can be $-(CH_2)_4-$, $-(CH_2)_5-$ or $-(CH_2)_6-$); and $L^1$ and $L^2$ are hydrocarbon linking groups, for example, a linear or branched chain alkyl of the formula $-(C_nH_{2n})-$ wherein n is, for example, 1 to 8 in the case of $L^1$ and 2 to 8 in the case of $L^2$ except when A is $-PO_3H$ or $-SO_3H$ in which case n can be 1–8; a cycloalkyl of 3 to 8 carbon atoms, preferably 5 or 6 carbon atoms; or an interphenylene Advantageously, $L^1$ and $L^2$ are —$(C_nH_{2n})$— wherein n is 1 to 8 in the case of $L^1$ or 2 to 8 in the case of $L^2$ except when A is —$PO_3H$ or —$SO_3H$ in which case n can be 1–8 (examples of branched chain alkyls include —$CH_2CHR$—, —$CH_2CHRCH_2$—, —$CHRCH_2CH_2$—, and —$CH_2CH_2CHR$— wherein R is an alkyl group and wherein the total number of carbon atoms, including R, does not exceed 8).

A particular group of compounds of the invention is of the formula (I) wherein A, $R^1$, $R^2$, $L^1$ and $L^2$ are as defined above in said first embodiment with the proviso that when A is —$SO_3H$ or pharmaceutically acceptable salt thereof or physiologically hydrolyzable derivative thereof, one of $R^1$ and $R^2$ is H, and $L^1$ and $L^2$ are $(CH_2)_2$, then the other of $R^1$ and $R^2$ is not H.

Another particular group of compounds of the invention is of the formula (I) wherein A, $R^1$, $R^2$, $L^1$ and $L^2$, are as defined above in the first embodiment with the proviso that when A is —$SO_3H$ or pharmaceutically acceptable salt thereof or physiologically hydrolyzable derivative thereof, one of $R^1$ and $R^2$ is H, and $L^1$ and $L^2$ are $(CH_2)_2$, then the other of $R^1$ and $R^2$ is not $C_6H_5CH_2OCO$—.

A further particular group of compounds of the invention is of the formula (I) wherein A is a group of the formula —$PO_3H$ or —$OPO(OH)_2$, more particularly —$PO_3H$, or a pharmaceutically acceptable salt thereof or a physiologically hydrolyzable derivative thereof, and wherein $R^1$, $R^2$, $L^1$, and $L^2$ are as defined above in the first embodiment.

Another particular group of compounds of the invention is of the formula (I) wherein A is a group of the formula —$SO_3H$ or —$OSO_2OH$, more particularly —$OSO_2OH$, or pharmaceutically acceptable salt thereof, or physiologically hydrolyzable derivative thereof, and wherein $R^1$, $R^2$, $L^1$ and $L^2$ are as defined above in the first embodiment. The provisos above can apply to this group of compounds as well.

A further particular group of compounds of the invention is of the formula (I) wherein at least one of $R^1$ and $R^2$ is an alkyl, advantageously a lower alkyl (eg $C_1$ to $C_6$), and wherein A, $L^1$, $L^2$ and the other of $R^1$ and $R^2$ are as defined above in the first embodiment.

Another particular group of compounds of the invention is of the formula (I) wherein $R^1$ is an alkyl and $R^2$ is acyl and wherein A, $L^1$ and $L^2$ are as defined above in the first embodiment.

A further particular group of compounds of the invention is of the formula (I) wherein $L^1$ is —$(CH_2)$— and wherein A, $R^1$, $R^2$, and $L^2$ are as defined above in the first embodiment.

Yet another particular group of compounds of the invention is of the formula (I) wherein $R^1$ and $R^2$ are taken together and form, with the nitrogen to which they are attached, a 5 to 7 membered ring, and wherein A, $L^1$ and $L^2$ are as defined above in the first embodiment.

The present compounds can also be present covalently bound to proteins, for example, antigens or other immunologically active proteins, or cell targeting proteins. Such conjugates can be synthesized using techniques known in the art.

The compounds of the present invention can be prepared using, for instance, methods provided in the Examples and in U.S. Pat. No. 4,102,948 and U.S. Pat. No. 4,218,404, as appropriate.

In another embodiment, the present invention relates to methods of using the above-described compounds in vivo and in vitro to alter (eg increase) cellular productivity and vitality and to modulate cellular differentiation, growth and/or function.

In vivo, the compounds can be used to elicit a variety of responses, including simulating bone marrow and platelet production, stimulating erythropoiesis, altering (eg increasing) immunogenic responsiveness and treating neoplasia. For example, the present compounds can be used to treat anemia and neutropenia. The compounds of the invention can be used to treat or prevent premature aging and degenerative diseases and to treat inherited metabolic diseases. The compounds of the invention can be used in the treatment of diseases of immune dysfunction including, without limitation, autoimmune diseases such as rheumatoid arthritis, diabetes, thyroiditis, lupus (SLE), connective tissue diseases, multiple sclerosis, sarcoidosis, psoriasis, hepatitis, and kidney diseases. The compounds can be used, for example, in the treatment of genetic diseases of aging (Ataxia telangieccasia, progeria and Werner's syndrome), in accelerated aging (as compared to the ultimate biologic potential of the organism), and in the treatment of Alzheimer's disease. The present compounds can be used to delay sensecence of fibroblasts, neural, lymphoid, epithelial, endothelial, mesenchymal, neuroectoderm, mesothelial and other cells, and to maintain function and health of aged cells and organisms.

The compounds can be used to cause an alteration in the number of cells of a particular cell type (eg epithelial cells or mesenchymal cells) (the compounds can be used, for example, to increase the number of red cells or white cells or the numbers of neuronal cells) or to cause an alteration in cellular function (eg an increase phagocytic activity of macrophage).

From the standpoint of immunogenic responsiveness, the present compounds can be used to enhance antigen processing, cell to cell communication, cellular immunity, natural immunity, humoral immunity, macrophage function, NK cell function, immune surveillance, immune response and immune killing. Further, the compounds of the invention can be used in conjunction with vaccination protocols to alter (eg increase) the response elicited by an antigen or an immunogenic conjugate. The present compounds can be used in vaccinations against infectious, neoplastic, autoimmune and other diseases. Specifically, the present invention can be used to enhance vaccinations to bacterial and viral diseases, for example, pneumonia, meningitis, TB, hepatitis B and HIV and to parasitic diseases. Further examples include bacterial diseases: *Pyogenic cocci* (staphylococci, pharyngitis, tonsillitis, sinusitis, streptococci, pneumococci, meningococci, gonococci), enteric bacilli (*Escherichia coli,* Klebsiella, *Salmonella shigella*), cholera, pseudomonas (*Pseudomonas aeruginosa, Pseudomonas mallei*), bacteroides, mycobacteria (tuberculosis), spirochetes (*Treponema pallidum* (syphilis)), clostridia, *Diphtheria hemophilues* and *Bordetella bacilli, Granuloma inguinale,* brucella, tularemia, anthrax, plague, mycoplasma, listeriosis; rickettsial disorders: typhus group, Rocky Mountain spotted fever, Lyme disease, scrub typhus, Q fever; chiamydial disorders: trachoma and inclusion conjunctivitis, lymphogranuloma venereum, and psittacosis; viral diseases: cutaneous viral infections (chickenpox, herpes zoster, measles), respiratory viral infections, viral diseases of the central nervous system, viral diseases of the liver, viral diseases of the salivary glands, and infectious mononucleosis; fungal diseases: candida albicans, mucor, histoplasmosis, aspergillosis, blastomycosis, coccidicidomycosis, actinomycosis and nocardiosis; and protozoal (parasitic) diseases: pneumocystosis, amebiasis, malaria, toxoplasmosis, leishmaniasis, trypanosomiasis, and giardiasis; helminths diseases (worms): trichinosis, strongyloidiasis, enterobius vermicularis, filariasis, hookworm disease, ascariasis, flukes, cestodes, tapeworms, and trichuriasis; and ocher diseases: sarcoidosis, cat-scratch disease, legionnaires' disease.

The compounds of the invention can also be used to inhibit the toxicity associated with immunotoxic and carcinogenic agents.

Depending on the effect sought and the clinical situation, the compounds of the invention can be administered before, during or after vaccination. Use of the present compounds can result in more effective injections and/or a reduction in the number of injections necessary for vaccination. The present compounds can also be used to treat infections, including chronic infections.

In a specific embodiment, the invention relates to a method of effecting isotype conversion using the compounds of the present invention. As shown in Example IX, the present compounds can be used to effect rapid induction of immunoglobulin G. These data demonstrate that the present compounds can be used to elicit a rapid response to a vaccine thereby reducing the number of injections necessary and/or increasing the efficiency of the each injection. The compounds of the invention can also focus antibody production of the polysaccharide and thus effect excellent responses to polysaccharide antigens, whether or not conjugated to a protein carrier.

As to neoplasia treatment, the compounds of the invention can be used to treat a variety of preneoplastic and neoplastic conditions, including both soft (eg hematolymphoid) and solid tumors (eg carcinomas and sarcomas). More specifically, the compounds of the invention can be used to treat breast cancer, prostate cancer, glioblastomas, melanomas, myelomas, lymphomas, leukemias, lung cancer, skin cancer, bladder cancer, kidney cancer, brain cancer, ovarian cancer, pancreatic concer, uterine cancer, bone cancer, colorectal cancer, cervical cancer and neuroectodermal cancer, and premalignant conditions, including, without limitation monoclonal gammapothies, dysplasia, including, without limitation, cervical and oral dysplasia. The compounds can also be used to treat conditions associated with altered differentiation (eg loss of pigmentation, hair, alteration of skin including psoriasis; alteration of gastrointestinal, kidney, liver, brain, endocrine, immune, lung, connective tissue, cardiac or other organ function).

The compounds of the invention can be administered topically, orally, rectally, intravaginally intravenously, intraperitoneally, subcutaneously, intramuscularly or intranasally, as appropriate for the effect sought. The compounds can also be administered transdermally using, for example, transdermal patches or transmucosally via sprays or other application.

Dosages of the present compounds can range, for example, from femtograms/kg b.w. to nanograms/kg b.w. in the case of disease prevention or function/health improvement to about 10 $\mu$g/kg b.w. to about 100 mg/kg b.w. in disease treatment regimens. Optimum doses for any particular situation can be determined by one skilled in the art without undue experimentation, often using appropriate in vitro or animal models.

The compounds of the invention are typically used in the form of a pharmaceutical composition comprising the compound of formula I, or salt or hydrolyzable derivative thereof as described above, together with a pharmaceutically acceptable diluent or carrier. The composition can be present in dosage unit form, for example, as a tablet, capsule or suppository. The composition can be formulated so as to be suitable for topical application (eg as a gel, cream, lotion or ointment). Alternatively, the composition can be present as a solution or suspension (eg sterile) suitable for administration by injection, inhalation, intranasally or dropwise to the eye or other sites as appropriate. The compound of the invention can be prepared as a slow release formulation appropriate for internal or external use. Using techniques known in the art, the compounds of the invention can also be trapped in or bound to a polymer, a solid support, a liposome or a gel.

Carriers and diluents known in the art can be used and the composition, when, for example, in the form of a tablet or capsule, can be formed with an enteric coating.

The composition of the invention can include active agents in addition to the compounds of formula I. Examples of such additional active agents include cancer chemotherapeutic agents, hormones, vitamins, cytokines, enzyme regulators, regulatory macromolecules, regulatory thiols or other small molecules.

The present compounds also have ex vivo applications including in the growth, maintenance or differentiation of tissue grafts, including bone and vascular grafts, and in the treatment of cells and organs, for example, prior to transplantation or use in the laboratory.

While the compounds of the invention are suitable for therapeutic use in humans, the compounds of formula I are also useful in the veterinary treatment of similar conditions affecting warm-blooded animals, such as dogs, cats, horses and cattle. For such purposes, the compounds of the formula I can be administered in an analogous amount and manner to those described above for administration to humans. The compounds of the invention also have application to lower organisms, including insects, reptiles, birds, fish and plankton, microorganisms, or others. They can be used in aqueous environments, including in marine or fresh water settings. For example, the present compounds can be used to alter (eg stimulate) fish growth, development and/or reproduction, for example, in aqua cultures.

In addition to the usefulness of the present compounds in connection with intact animals (particularly, but not exclusively, mammals) cells, tissues and organs, the compounds of the invention also have application in agricultural settings to alter (eg stimulate) plant growth and development as well as plant cell function and productivity. The compounds of the invention can be applied to the plant or soil using ary of a variety of known protocols. The present compounds can be used alone or in combination with other sprays, fertilizers or injections.

Specific in vitro uses of the present compounds include facilitating adaptation to culture, maintenance of differentiation and function, stimulating cellular productivity and increasing cellular vitality. Cell types susceptable to the effects of the present compounds include eucaryotic cells, for example, from mammalian tissue or from insect or arachnid tissue, as, well as cells derived from plant tissue and fungal (eg yeast) cells. Procaryotic cells, including bacterial cells, can also be used.

Cells can be grown or stored in the presence of the present compounds using any of a variety of available technique, including growth on plastic or glass or other support (eg beads or hollow fibers), growth in suspension (eg in liquid or semisolid medium), growth in a bioreactor, or storage in a frozen or dried state. Primary cultures or serial cultures, or otherwise, can be used.

As indicated above, the compounds of the invention can be used, as appropriate, to alter cell viability/vitality and/or productivity. Altered viability/vitality can be manifest, for example, as a delay in senescence or altered adaptability to culture. Altered productivity can be manifest, for example, by an alteration in the production of a cell specific product, eg a protein, for example, an alteration in hybridoma production of antibodies. The compounds of the invention can also be used to stimulate host cell production of recombinant or natural proteins or activities. The compounds of the invention can also be used in whole cell or cell free environments to stimulate or control biochemical reactions including replication, transcription, translation, transport or modification of structural or enzymatically active molecules or organelles.

The amount of the compound of the invention to be used and the frequency of exposure can be readily determined by one skilled in the art and will vary with the cell type, the compound used and the effect sought In determining optimum concentrations, appropriate an vitro assays are run in the femtogram/ml to 10's of mg/ml range.

Various aspects of the present invention are described in greater detail in the non-limiting Examples that follow. Certain of the synthetic procedures described below correspond to those described by Knight: et al, Cancer Research 54:5623 (1994) or in U.S. Pat. No. 4,218,404, or represent modifications thereof. In addition, the disclosures of WO 92/00955 and PCT/US91/04725 are relevant here, including the portions therein that relate to syntheses, therapeutic regimens and cell culture treatment protocols, those regimens and protocols being applicable to the compounds of the present invention.

EXAMPLE I

Synthesis of N-Carbobenzoxy-$\beta$-Alanyl-Taurine Zinc Salt

Method I
Preparation of N,N'-bis(CBZ)-$\beta$-Alethine from N-CEZ-$\beta$-alanine To a 250 ml round bottom flask were added a stir bar, N-CBZ-alanine (5.805 g, 26.008 mmol), N-hydroxysuccinimide (2.993 g, 26.008 mmol, 1 eq.), and 1,3-dicyclohexylcarbodiimide (5.366 g, 26.008 mmol, 1 eq.). The flask was sealed with a septum and purged with argon. $CH_2Cl_2$ (86 ml) was then added and the mixture stirred overnight at room temperature (rt) . All of the solids did not dissolve upon addition of $CH_2Cl_2$. The solids were then removed via vacuum filtration through a pre-argon-purged medium glass fritted buchner funnel. The funnel was equipped with an argon purge funnel and a 500 ml round bottom flask containing a stir bar and cystamine•2HCl (1.464 g, 6.502 mmol, 0.25 eq.). The flask and solids (white) were then rinsed with 3×15 ml $CH_2Cl_2$. The filtrate was colorless to light yellow. The flask was removed from the buchner, sealed with a septum and purged with argon. To the stirring solution was added $Et_3N$ (2.9 ml, 20.806 mmol, 0.8 eq.) All of the solids did not dissolve. The reaction was stirred overnight at room temperature. The product was then collected using an 11 cm buchner funnel with #541 Whatman filter paper. The flask and solids (white) were rinsed with 3×15 ml $CH_2Cl_2$. The filtrate was colorless to yellow. The solids were placed in a 250 ml round bottom flask and dried under high vacuum overnight. The crude product weight was determined and DMSO (0.3 g/ml) was added and heated to 70° C.–90° C. to dissolve the solids with the aid of stirring. $H_2O$ (0.12 g/ml) was then added slowly with vigorous stirring. The mixture was cooled to room temperature and collected after 3 hours using an 11 cm buchner funnel with #541 Whatman filter paper. The solids (white) and flask were rinsed 3×15 ml $CH_2Cl_2$ $H_2O$ followed by 2×15 ml EtOAc. The solids were chopped-up with a spatula and dried under high vacuum in a 250 ml round bottom flask. The recovery was 3.568 g corresponding to a 97.5% yield.
Preparation of N-carbobenzoxy-$\beta$-alanyl-taurine zinc salt from N,N'-bis(CPZ)-$\beta$-alethine (small additions of ZnO or $Ca(OH)_2$)

To a 250 ml erlenmeyer flask were added a stir bar, N,N'-bis(CBZ)$\beta$-alethine (2.524 g, 4.486 mmol), dimethylsulfoxide (2.5 ml), N,N-dimethylformamide (2.5 ml), pyridine (3.2 ml), $CHCl_3$ (75 ml), and $H_2O$ (150 ml). The mixture was stirred vigorously giving an emulsion (not all solids dissolved). A pH meter was immersed in the aqueous phase. The pH was near 7.3 to 7.7. $I_2$ (7.97 g, 31.401 mmol, 7 eq.) was then added. Initially the organic phase was red and the aqueous phase was colorless. During the reaction, the color of the aqueous phase darkened to red and the emulsion subsided. The pH dropped to 5.7 within 10 minutes of adding $I_2$. ZnO (100–200 mg, 0.3–0.6 eq.) was added in portions to keep the pH between 5.7 and 6.0. After ~3.5 hours, the pH stabilized and the reaction was allowed to stir for an additional 2 hours (5.5 h total reaction time). The phases were separated (organic was dark red) and the aqueous phase was washed with 10 ml $CHCl_3$. The aqueous phase (light red) was extracted additionally with $CHCl_3$ using a continuous liquid/liquid extractor overnight. The aqueous phase (colorless to very light pink) was separated, partially evaporated on a rotary evaporator to remove dissolved organics, shelf frozen, and lyophilized. The residue (golden brown) was dissolved in 1 ml $H_2O$ and 3 ml acetonitrile and added to 100 ml acetonitrile. The white precipitate was collected on a #541 Whatman filter paper and rinsed with 40 ml acetonitrile. The recovery was 1.676 g of white solids corresponding to a 52% yield (N-carbobenzoxy-$\beta$-alanyl-taurine zinc salt).
Preparation of N-carbobenzoxy-$\beta$-alanyl-taurine zinc salt from N,N'-b-s(CBZ)$\beta$-alethine (ZnO added initially)

To a 125 ml erlenmeyer flask were added a stir bar, N,N'-bis(CBZ)$\beta$-alethine (809 mg, 1.438 mmol), dimethylsulfoxide (0.8 ml), N,N-dimethylformamide (0.8 ml), pyridine (1.0 ml), $CHCl_3$ (24 ml) , $H_2O$ (80 ml) and ZnO (526 mg, 6.470 mmol, 4.5 eq.). The mixture was stirred vigorously giving an emulsion (not all solids dissolved). $I_2$ (3.28 g, 12.904 mmol, 9 eq.) was then added. Initially, the organic phase was red and the aqueous phase was colorless. During this reaction, the color of the aqueous phase darkened to red and the emulsion subsided. The mixture was stirred overnight. The phases were then separated (organic was dark red) and the aqueous washed with 20 ml $CHCl_3$. The aqueous phase (light red) was extracted additionally with $CHCl_3$ using a continuous liquid/liquid extractor overnight. The aqueous phase (colorless to very light pink) was separated, partially evaporated on a rotary evaporator to remove dissolved organics, shelf frozen, and lyophilized. The residue (golden brown) was dissolvec in 0.5 ml $H_2O$ and 2 ml acetonitrile and added to 75 ml acetonitrile. The white precipitate was collected on a #541 Whatman filter paper and rinsed with 20 ml acetonitrile. The recovery was 630 mg of white solids, corresponding to a 61% yield (N-carbobenzoxy-$\beta$-alanyl-taurine zinc salt).

Figure 2:
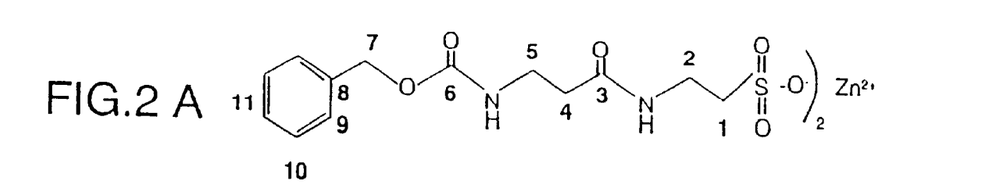
FIG. 2 shows specific compounds of the invention bearing carbon designations.
Figure 3A:
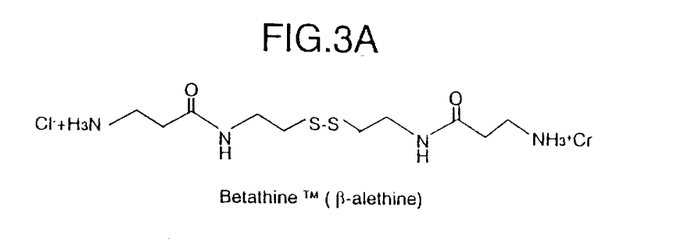
FIG. 3 shows specific compounds of the invention.
Figure 3B:
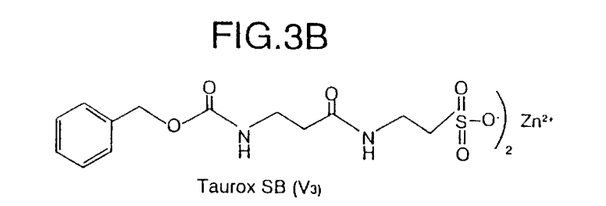
Figure 3C:
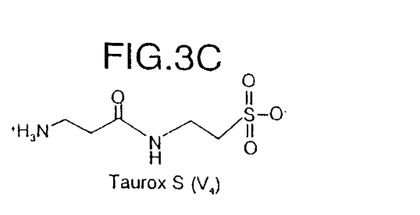
Figure 3D:
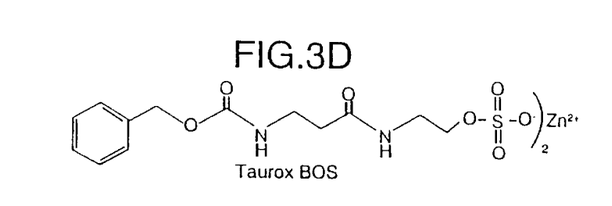
Figure 3E:
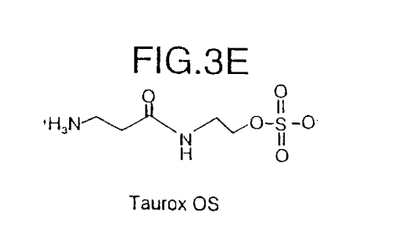
Figure 3F:
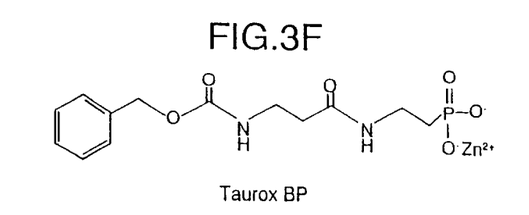
Figure 3G:
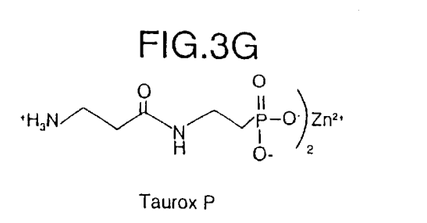
Figure 3H:
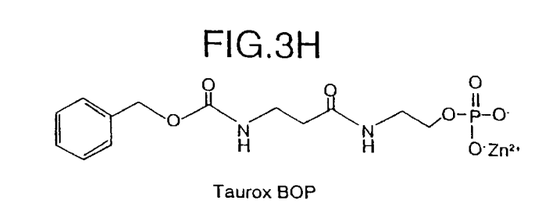
Figure 3I:
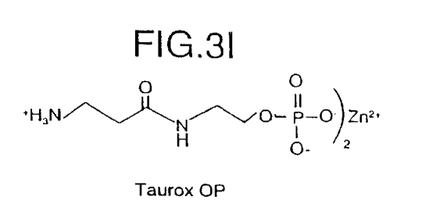

The $^{13}$C NNR spectral data were as follows (for numerical assignment see FIG. 2A):

| Signal | DMSO solvent:C—H coupled |
|---|---|
| 1 | 48.4 |
| 2 | 33.8 |
| 3 | 172.2 |
| 4 | 34.6 |
| 5 | 36.4 |
| 6 | 156.4 |
| 7 | 65.4 |
| 8 | 135.0 |
| 9 | 125.8 |
| 10 | 126.5 |
| 11 | 128.0 |

Method IIa

Figure 1A:
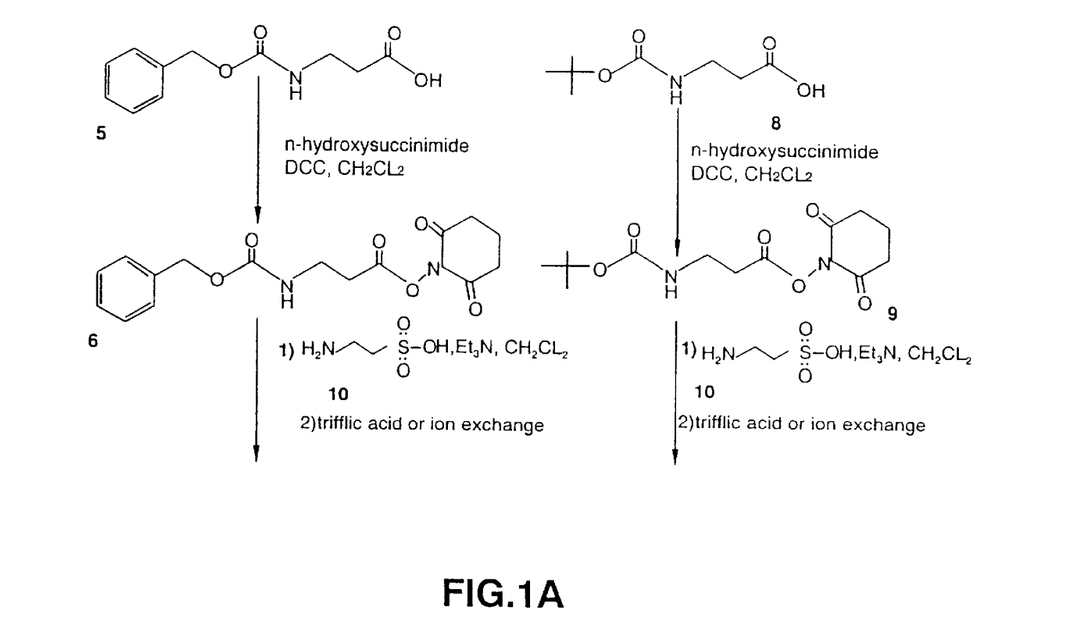
FIG. 1 shows synthetic reaction schemes.
Figure 1B:
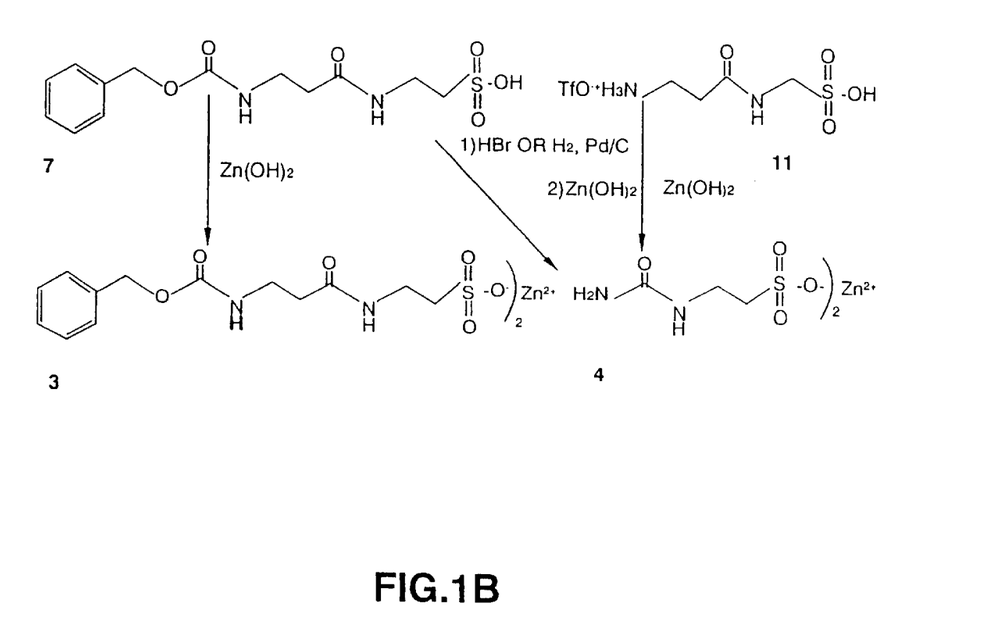

Preparation of N-carbobenzoxy-β-alanyl-taurine (free acid and zinc salt) from N-(CEZ)-β-alanine The N-(CBZ)-β-alanine (563 mg, 2.522 mmol), N-hydroxysuccinimide (290 mg, 2.522 mmol) and DCC (520 mg, 2.522 mmol) were dissolved (no obvious dissolution) in $CH_2Cl_2$ (11.5 ml, to make a 0.22 M solution). The reaction was allowed to mix overnight at room temperature. The crude reaction mixture was filtered through a sintered glass funnel to remove the dicyclohexylurea (DCU). The reaction was filtered "anhydrously" into a flask containing 316 mg (2.522 mmol) taurine. The filter cake was washed with. 3, 5 ml volumes of $CH_2Cl_2$. After adding 316 μl $Et_3N$ (1 eq), the reaction was allowed to mix at room temperature. The reaction was allowed to mix until complete by NMR. The crude reaction mixture was purified by trituration with MeCN. The crude reaction mixture was dissolved in 14 ml $CH_2Cl_2$ (0.2 M) and 1 eq of triflic acid was added. The reaction was allowed to mix overnight at room temperature although the reaction appeared complete after mixing for only 15–20 minutes. The reaction mixture was filtered and the filter cake washed with $CH_2Cl_2$. The filter cake (the free acid) was divided into two portions. One portion (305 mg) and 0.5 eg $Zn(OH)_2$ were dissolved in 5 ml $H_2O$ and allowed to mix for 1 hour and then it was concentrated by lyophilization to give 340 mg as a white solid (66% based on starting N-(CEZ)-β-alanine). The other portion was purified and characterized as the free acid (190 mg). NMR data were obtained on both the free acid and the Zn salt, the Zn salt being the more pure (see FIG. 1 for reaction scheme).

The $^1$H NMR spectral data were as follows (for alphabetical assignment see FIG. 2B):

| Signal | D$_2$O solvent |
|---|---|
| a | 2.99 (t, J = 12.8 Hz, 2 H) |
| b | 3.48 (t, J = 12.8 Hz, 2 H) |
| c | not seen due to hydrogen bonding |
| d | 2.38 (t, J = 12.4 Hz, 2 H) |
| e | 3.35 (m, 2 H) |
| f | not seen due to hydrogen bonding |
| g | 5.07 (m, 4 H) |

The $^{13}$C NMR spectral data were as follows (for numerical assignment see FIG. 2A):

| Signal | DMSO solvent |
|---|---|
| 1 | 51.1 |
| 2 | 36.1 |
| 3 | 170.2 |
| 4 | 36.4 |
| 5 | 37.7 |
| 6 | 156.6 |
| 7 | 65.7 |
| 8 | 137.8 |
| 9 | 128.3 |
| 10 | 128.9 |
| 11 | 128.9 |

Method IIb

Preparation of N-carbobenzoxy-β-alanyl-taurine (Free Acid and Zinc Salt) from N-(CBZ)-β-Alanine (Scale up)

In a three-neck 1 L flask was placed CBZ-β-alethine (48.2 g, 215.9 mmol) under $N_2$. To this was added freshly distilled methylene chloride (750 mL), followed by N-hydroxysuccinimide (24.85 g, 215.9 mmol). To the resulting suspension was added 1,3-dicyclohexylcarbodiimide (DCC, 44.54 g, 215.9 mmol). At this scale the reaction generated a noticeable exotherm, sufficient to reflux the $CH_2Cl_2$. The reaction mixture was stirred under $N_2$ for 5 hours at which point the mixture was filtered through a sintered glass buchner funnel. The filter cake was washed with $CH_2Cl_2$ (3×100 mL). To the filtrate was added taurine (27.03 g, 215.9 mmol) and triethylamine (33.1 mL, 237.5 mmol). The reaction was stirred under $N_2$ and monitored by $^1$H-NMR analysis. The reaction mixture was vacuum filtered through a buchner funnel using Whatman #542 filter paper. The filtrate was stripped to an oil using reduced pressure, then placed on high vacuum. The "oil" was triturated with acetonitrile with one drop off water to quench any unreacted DCC. The mixture was filtered and the MeCN was stripped off under reduced pressure then placed on high vacuum. The resulting oil was dissolved in water (50 mL). A curdy white precipitate formed, more water (150 mL) was added and the resulting solid was filtered off. In the filtrate an oil precipitated out of solution. $^1$H-NMR spectra were obtained to determine the location of product. The product was in the aqueous layer as expected. The aqueous phase containing the product was then eluted through a H+ ion exchange column. Fractions (225 mL) were collected and spotted on TLC. The desired product was found in fractions 2–7. These fractions were combined and the water removed under reduced pressure. To the resulting oil was added MeCN (1 L) and the solution was stirred. The remaining water was removed by azeotropic distillation with the MeCN. The resulting solid was collected by vacuum filtration and washed with MeCN. The solid was vacuum dried in a 1 L round bottom flask then transferred to a tared 4 oz. amber bottle. Final package weight was 38.89 g (117.7 mmol, 54.5% yield). The zinc salt was prepared by treatment with $Zn(OH)_2$ in $H_2O$, followed by lyophilization. The spectral data for the product matched exactly a standard sample of N-carbobenzoxy-β-alanyl-taurine zinc salt.

EXAMPLE II

Synthesis of β-Alanyl-Taurine (Free Acid and Zinc Salt)

N-carbobenzoxy-β-alanyl-taurine (1.00 g, 3.4 mmol) was slurried in 23 ml glacial AcOH. To the mixture was added 3.4 mL HBr in AcOH (30 wt %) to result in a clear solution. The reaction was heated to 40° C. and allowed to mix overnight. The product precipitated out of solution and acetcnitrile was added to force the precipitation. The mixture was filtered, the filter cake washed and the product collected. The crude Br salt was loaded onto an ion exchange column (Dowex AG1-XB8). The column was eluted with $H_2O$. The product cut was collected and lyophilized to give 583 mg of β-alanyl-taurine (87.3%). The zinc salt was prepared by treatment with $Zn(OH)_2$ in $H_2O$, followed by lyophilization. (See FIG. 1 for reaction Scheme.)

The $^1H$ NMR spectral data were as follows (for alphabetical assignment see FIG. 2C):

| Signal | $D_2O$ solvent |
| --- | --- |
| a | 3.09 (t, J = 12 Hz, 2 H) |
| b | 3.59 (t, J = 12 Hz, 2 H) |
| c | not seen due to hydrogen bonding |
| d | 2.66 (t, J = 12 HZ, 2 H) |
| e | 3.25 (t, J = 12 Hz, 2 H) |

The $^{13}C$ NMR spectral data were as follows (for numerical assignment see FIG. 2D):

| Signal | DMSO solvent |
| --- | --- |
| 1 | 50.3 |
| 2 | 36.2 |
| 3 | 169.6 |
| 4 | 33.1 |
| 5 | 36.2 |

For comparison, β-alanyl-taurine zinc salt prepared using the method of Knight et al, Cancer Research 54:5623 (1994) gave the following $^1H$ NMR spectra (for alphabetical assignment see FIG. 2C):

| Signal | $D_2O$ solvent |
| --- | --- |
| a | 2.93 (t, J = 12 Hz, 2 H) |
| b | 3.42 (t, J = 12 Hz, 2 H) |
| c | not seen due to hydrogen bonding |
| d | 2.50 (t, J = 12 Hz, 2 H) |
| e | 3.10 (t, J = 12 Hz, 2 H) |

EXAMPLE III

Preparation of N-Carbobenzoxy-β-Alanyl-Ethanolamine Phosphate (Free Acid and Zinc Salt) from N-(CBZ)-β-Alanine N-(CBZ)-β-alanine (274 mg, 1.23 mmol), N-hydroxysuccinimide (141 mg, 1.23 mmol) and dicyclohexylurea (DCC, 253 mg, 1.23 mmol) were dissolved in tezrahydrofuran (THF, 4.1 mL). The reaction was allowed to mix at room temperature overnight before being filtered to remove the dicyclohexylurea (DCU). To the filtrate, a solution of 2-aminoethyl dihydrogen phosphate (1.23 mmol) in $H_2O$ (0.5 ml) was added. To the reaction mixture was added 2.1 molar equivalents of triethylamine. The reaction was allowed to mix for three days before the THR was removed under vacuum. The remaining aqueous phase was filtered and loaded onto a prepared ion exchange column (Dowex AG 50W-X8). The column was eluted with water. The product fractions were collected and lyophilized. The crude solid (260 mg) was treated with 1.0 molar equivalents of $Zn(OH)_2$ in $H_2O$ to make the salt. The crude solid (after lyophilization) was triturated with acetronile and collected (50 mg).

EXAMPLE IV

Synthesis of N-Carbobenzoxy-β-Alanyl-Aminoethylphosphonic Acid (Free Acid and Zinc Salt) from N-(CBZ)-β-Alanine N-(CBZ)-β-alanine (301 mg, 1.35 mmol), N-hydroxysuccinimide (155 mg, 1.35 mmol) and dicyclohexylurea (DCC, 278 mg, 1.35 mmol) were dissolved in tetrahydrofuran (THF, 4.5 ml). The reaction was allowed to mix at room temperature overnight before being filtered to remove the dicyclohexylurea (DCU). To the filtrate, a solution of 2-aminoethylphosphonic acid (1.35 mmol) in $H_2O$ (0.5 ml) was added. To the reaction mixture was added 2.1 molar equivalents of triethylamine. The reaction was allowed to mix for three days before the THF was removed under vacuum. The remaining aqueous phase was filtered and loaded onto a prepared ion exchange column (Dowex AG 50W-X8). The column was eluted with water. The product fractions were collected and lyophilized. The crude solid (270 mg) was treated with 1.0 molar equivalents of $Zn(OH)_2$ in $H_2O$ to make the salt. The crude solid (after lyophilization) was triturated with acetonitrile and collected (50 mg).

EXAMPLE V

In Vitro Simulation of Differentiation and Production of Differentiated Product by N-Carbobenzoxy-β-Alanyl-Taurine Zinc Salt Hybridoma cells (ATCC #CRL-8014, OKT-8, secreting an IgG2 anti-human T-cell subset antibody) were growth with or without N-carbobenzoxy-β-alanyl-taurine zinc salt in T25 culture flasks. Cells were inoculated at a density of 10,000 cells/ml and maintained below 500,000 cells/ml in 5 mls of protein-free media containing HyQ-PF-MAB from Hyclone. Aliquots were assayed for Mab production by a sandwich ELISA. Aliquots were diluted to be within the standard range and added to plates precoated with goat anti-mouse IgG by incubating two hours at room temperature. Wells were washed and reacted with diluted supernatants, then washed and detected with peroxidase labeled anti-mouse antibodies. The results are shown in Table 1.

TABLE 1

Altered Production of Monoclonal Antibodies from Hybridomas

| Drug | 1 gG, µg/ml | IgG, pg/cell |
| --- | --- | --- |
| 0-control | 12 | 41.7 |
| N-carbobenzoxy-β-alanyl-taurine 200 pg/ml | 50 | 80.6 |
| Increase | 316% | 93% |

EXAMPLE VI

Stimulation of ProteIn Production from Mammalian Cells

CHO cells containing a cloned gene for tissue plasminogen activator (tPA) were obtained from ATCI as # CRL-9606. The tPA gene had been introduced by transfection of a plasmid pETPFP. The cells were propogated in T-25 flasks in Ham's F-12 medium with 10% fetal bovine serum. The cell cultures were innoculaitedi by adding 5 ml of cells at $2 \times 10^4$ cells/ml into T-25 flasks.

The effect of N-carbobenzoxy-β-alanyl taurine zinc salt on the production of tPA was tested by adding this compound to the growth medium, and maintaining the indicated levels of the compound over many (eg 6) passages of the cells.

At the end of log phase growth, the cultures were harvested by trypsinization. One ml was centrifuged to remove cells and the supernatant assayed for tPA in the IMUBIND total tPA Stripwell ELISA from American Diagnostica Inc.

The results shown in Table 2 demonstrate that the compound (N-carbobenzoxy-β-alanyl taurine zinc salt, #'s 1, 2 and 3 in Table 2) alters the per-cell production of tPA by about 2 fold. The cell numbers per milliliter were determined by direct counting of trypan-blue stained cells on a hemacytometer.

TABLE 2

| Compound | ELISA Optical Density | Supernatant Concentration nanograms/ml* | Culture Cell Density | Picograms tPA per cell |
|---|---|---|---|---|
| Control | 0.177 | 424.6 | 2.2 × 10⁵ | 1.93 |
| #1 1 pg/ml | 0.332 | 1,492.8 [3.5 × control] | 4.0 × 10⁵ | 3.73 [1.9 × control] |
| #2 1 pg/ml | 0.317 | 1,389.4 [3.3 × control] | 4.8 × 10⁵ | 2.89 [15 × control] |
| #3 1 pg/ml | 0.422 | 2,113.0 [5.0 × control] | 5.2 × 10⁵ | 4.06 [2.1 × control] |

*The standard curve is "Abs = 0.1154 + .029* Concentration", with a correlation coefficient of 0.9977.

EXAMPLE VII

In Vivo Coordinated T Cell Dependent Response Delayed Type Hypersensitivity

In order to test an in vivo coordinated T cell dependent response, delayed type hypersensitivity (DTH) was measured. DTH is the test used clincially to determine if a person has mounted an immune response to many antigens. The most frequent application is measurement of DTH in response to tuberculosis called a PPD or tine test. It is also used to determine if a patient, such as a cancer patient, has had a failure of the immune system and become anergic.

In the laboratory this test involves the generation of a specific response to a oxazalone (OX) in mice and measurement of the response. The generation of the response (sensitization or initial exposure) was caused by the application of OX to the shaved abdomen of the animal (50 μl of 1.2% OX in olive oil). Measurement of the response occurred 24 and 48 hours following application of OX (5 μl 1.2%) to the right ear of the animal. In the experiment performed, sensitization occurred on day 0; challenge occurred on day 4. On days five and six, the thickness of the ear was measured and the thickness before challenge was subtracted. The doses of OX used were chosen so that some normal untreated animals had a perceptible but moderate response to the OX at 24 hrs.

In order to measure the effect of N-carbobenzoxy-β-alanyl-taurine zinc salt, various doses were injected iv on Day −2, 0, +2 and +4.

Ten animals were used per group. Drug dilutions are made up and coded at one facility and an independent contract facility (Midlantic Research) performed all procedures in a "blind" fashion. In no case did control ears (those either not sensitized or not challenged) have swelling over 40 μ. Animals with 50 μ to 99 μ swelling were rated as having moderate swelling. Three control (saline injected) animals mounted a moderate response on at 24 hrs as expected. N-carbobenzoxy-β-alanyl taurine altered the response rate to eight of ten in two different treatment groups (this is above the 95% confidence bounds for an altered response by relative risk measure). All groups of animals receiving between 1 fg/kg and 1 mg/kg had more moderate responders than the saline injected group.

Those animals with 100 μ or greater swelling were rated as having major immune responses. No saline injected animal had major immune response az 24 hours while a total of 14 N-carbobenzoxy-β-alanyl-taurine treated animals had major immune response. One non drug treated animal had a major response at either 24 or 48 hours post challenge, while 21 N-carbobenzoxy-β-alanyl-taurine treated animals had a major response at one of these times. The data are presented in Table 3.

TABLE 3

N-carbobenzoxy-β-alanyl taurine Increases DTH
Percent of Animals with DTH

| Dose/kg> | 0 | 1 fg | 32 fg | 1 pg | 32 pg | 1 ng | 1 μg | 1 mg |
|---|---|---|---|---|---|---|---|---|
| Moderate DTH at 24 hrs | 30 | 70 | 60 | 50 | 80* | 80* | 40 | 70 |
| Major DTH at 24 hrs | 0 | 20 | 20 | 10 | 10 | 20 | 10 | 50* |
| Major DTH at 48 hrs. | 0 | 20 | 20 | 10 | 10 | 20 | 10 | 50 |
| Major DTH at either 24 or 48 hrs. | 10 | 20 | 20 | 10 | 40 | 20 | 30 | 60 |

*Relative Risk (RR) compared to control exceeds 1 even at lowest end of 95% confidence bounds. RR not tested at 48 hours

EXAMPLE VIII

Blood Cell Stimulation

A 96-well-based suspension culture system (Warren et al, Stem Cells 13:167 (1995) for human hematopoietic progenitor cells was used to monitor the commitment and differentiation of CD34+ cells in vitro. Expression of maturation and lineage markers on the cells in culture were measured by ELISA. The CD34+ cells were isolated from umbilical cord blood (90% purity) and grown in liquid culture in 96-well plates (2000 per well) for 10 days. A combination of growth factors was added that stimulates the expression of the appropriate lineage markers. The culture consisted of: IMDM plus 15% FBS, 0.5 ng/ml IL-3, 20 ng/ml SCF, 1 unit/ml EPO, 1 ng/ml GCSF and the indicated concentrations of test compounds. The cells were then fixed with a glutaraldehyde-paraformaldehyde mixture, attaching the cells firmly to the plastic. An ELISA was performed (Warren et al, Stem Cells 13:167 (1995)), using appropriate primary antibodies directed against cell surface markers. The expression of three different lineage markers was measured: CD14 (monocyte), CD15 (neutrophil), and glycophorin A (erythroid). The results are presented in Table 4.

TABLE 4

Increase in Blood Cell Production
Percent difference (relative to control)

| | Study 1:1 ng/ml compound | | | Study 2:1 ug/ml | | |
|---|---|---|---|---|---|---|
| Compound | monocytes | neutrophils | red blood cells | CD34 cells | monocytes | RBC |
| Taurox-BP | 18 | 14 | 1 | 0 | 2 | 4 |
| Taurox-BOP | 18 | 21 | 0 | 33 | 9 | 55 |
| Taurox-SB | 15 | 0 | 0 | not tested | | |
| Taurox-S | 47 | 55 | 50 | not tested | | |

Taurox-BP = N-carboxybenzoxy-β-alanyl aminoethylphosphonic acid
Taurox-BOP = N-carboxybenzoxy-β-alanyl-ethanolamine phosphate
Taurox-SB = N-carboxybenzoxy-β-alanyl-taurine
Taurox-S = β-alanyl-taurine
Study 2: same, expect 1700 cells per well

EXAMPLE IX

Immune Stimulation

BALB/c female mice (4–5 weeks of age) were pre-bled, then injected ip with 0.1 mls of indicted compounds on day −7, day −5, day −3, and day 0. On day 0, they received soluble polysaccharide antigen Pn14-Tetanus Toxin, 10 μg in 0.1 mls, given ip. Two other groups received Pn14-TT, 10 μg in 0.1 mls of a 60%; emulsion of complete Freund's adjuvant (CFA) on Day 0, given subcutaneously above the hind leg, just off the midline. The two CFA groups were treated indentically. All mice were bled on Day 4 and Day 14. On Day 84, mice were bled and boosted with 5 μf Pn14 (not conjugated to TT) and either the experimental compound or incomplete Freund's adjuvant (for those previously given CFA). Mice were bled on day 94. Sera at 1:1000 were analyzed by ELISA for anti-Pn14 antibodies. Prebleed values were subtracted.

| Mean Change in O.D. (Optical density, indicating presence of antibody) | | |
|---|---|---|
| | Change from pretest to 4 & 14 days after injection with antigen | Change from pre-boost 10 days after boost with UNCONJUGATED |
| Compound | Day 4 · Day 14 | polysaccharide |
| CFA (control) | −0.6 · 672 | −256 |
| CFA (control) | −1.0 · 367 | not tested |
| Taurox-BP, ng | 15.5 · 1399 | not tested |
| Taurox-BP, ug | 6.5 · 616 | not tested |
| Taurox-BP, mg | 3.3 · 924 | 187 |
| Taurox-BOP, ng | 5.4 · 877 | not tested |
| Taurox-BOP, ug | 1.8 · 515 | not tested |
| Taurox-BOP, mg | 0 · 366 | not tested |
| Taurox-SB, ng | 6.2 · 705 | not tested |
| Taurox-SB, ug | 3.9 · 483 | not tested |
| Taurox-SB, mg | 1.1 · 697 | 139 |
| Taurox-S, ng | 13.1 · 681 | 204 |
| Taurox-S, ug | 3.6 · 671 | not tested |
| Taurox-S, mg | 2.9 · 697 | not tested |

Notes
1. Values are the mean of 3 animals per drug/dose group.
2. Doses were 5 ng per kilogram of animal, 5 ug/kg, and 5 mg/kg of test compounds given prior to and with conjugated antigen, indicated above as "ng", "ug", and "mg"
3. CFA - Complete Freund's adjuvant, the current "gold standard vaccine adjuvant, but approved only for animal uses due to its toxicity. Two groups of 3 animals were used. Published data indicate CFA stimulates response 10x compared to saline.
Discussion
a. Only in animals treated with a compound of this invention is a 4-day response seen.
b. Only in animals treated with a compound of this invention is a response to unconjugated polysaccharide seen.
c. The 14-day response is greater with treatment.

EXAMPLE X

Syntheses

Synthesis of N-Carbobenzoxy-β-Alanyl-Ethanolamine Sulfate—Taurox BOS:

To a THF solution of N-(CBZ)-β-alanine and N-hydroxysuccinimide, add DCC. The reaction is mixed overnight at room temperature. The crude reaction mixture is filtered through a sintered glass funnel into a round bottom flask to remove the DCU that is formed. The activated ester should remain in solution. After concentrating and redissolving in solvent, ethanolamine or an alcohol protected derivative can be added as a solution to the solution containing the activated ester. Triethylamine can also be added. Workup of the reaction and purification results in formation of N-carbobenzoxy-β-alanyl-ethanolamine. The free alcohol can be sulfated by a variety of methods to result in formation of N-carbobenzoxy-β-alanyl-ethanolamine sulfate.

Synthesis of β-Alanyl-Ethanolamine Sulfate (from N-Carbobenzoxy-β-Alanyl-Ethanolamine Sulfate)—Taurox OS:

In a similar fashion to the conversion of N-carbobenzoxy-β-alanyl-taurine to 9-alanyl-taurine, N-carbobenzoxy-β-alanyl-ethanolamine sulfate can be converted to β-alanyl-ethanolamine sulfate. The conversion can be effected by slurrying the N-carbobenzoxy-β-alanyl-ethanolamine sulfate in glacial AcOH. To the mixture, HBr in AcOH (30 wt %) is added. The reaction can be heated and allowed to mix for a period of not less than 1 hour. The product can be isolated by usual workup and precipitation.

Synthesis of β-Alanyl-Ethanolamine Phosphate (from N-Carbobenzoxy-β-Alanyl-Ethanolamine Phosphate)—Taurox OP In a similar fashion to the conversion of N-carbobenzoxy-β-alanyl-taurine to β-alanyl-taurine, N-carbobenzoxy-β-alanyl-ethanolamine phosphate can be converted to β-alanyl-ethanolamine phosphate. The conversion can be effected by slurrying the N-carbobenzoxy-β-alanyl-ethanolamine phosphate in glacial AcOH. To the mixture, HBr in AcOH (30 wt%) is added. The reaction can be heated and allowed to mix for a period of not less than 1 hour. The product can be isolated by usual workup and precipitation.

Synthesis of β-Alanyl-Aminoethylphosphonic Acid (from N-Carbobenzoxy-β-Alanyl-Aminoethylphosphonic Acid)—Taurox P In a similar fashion to the conversion of N-carbobenzoxy-β-alanyl-taurine to β-alanyl-taurine, N-carbobenzoxy-β-alanyl-aminoethylphosphonic acid can be converted to β-alanyl-aminoethylphosphonic acid. The conversion can be effected by slurrying the N-carbobenzoxy-β-alanyl-aminoethylphosphonic acid in glacial AcOH. To the mixture, HBr in AcOH (30 wt %) is added. The reaction can be heated and allowed to mix for a period of not less than 1 hour. The product can be isolated by usual workup and precipitation.

Structures of the above compounds are shown in FIG. 3.

All documents cited above are hereby incorporated in their entirety by reference. The entire contents of U.S. Provisional Appln. 60/005,336, filed Oct. 17, 1995, is incorporated herein by reference.

One skilled in the art will appreciate from a reading of this disclosure that various changes in form and detail can be made without departing from the true scope of the invention.

What is claimed is:

1. A compound of the formula (I):

(I)

wherein:
A is a group of the formula —PO$_3$H, —SO$_3$H, —OPO—(OH)$_2$—OSO$_2$OH, or —SH, or pharmaceutically acceptable salt thereof or physiologically hydrolyzable derivative thereof,

R$_1$ is H, a linear or branched lower alkyl, an arylalkyl or an alkenyl,

R$_2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl, or $R^1$ and $R^2$ taken together form, with the nitrogen to which they are attached, a 5 to 7 membered ring, and $L^1$ and $L^2$ are, independently, a hydrocarbon linking group, a cycloalkyl, or an interphenylene, with the provisos that the compound of formula I is 4-amino N-(2-mercaptoethyl)butanamide or 3-amino N-(3-mercaptopropyl)propionamide;

or pharmaceutically acceptable salt thereof or unionized form thereof, and at least one of $R_1$ and $R_2$ is an alkyl or at least one of $L^1$ and $L^2$ is not —$(CH_2)_2$— or —$(CH_2)_3$—.

3. A compound of the formula (I):

wherein:

A is a group of the formula —$PO_3H$, or —$OSO_2OH$, or pharmaceutically acceptable salt thereof or physiologically hydrolyzable derivative thereof, $R^1$ is H, a linear or branched lower alkyl, an arylalkyl or an alkenyl, $R_2$ is H, a linear or branched lower alkyl, an alkenyl, an arylalkyl, an acyl, a carbonate ester, an allyloxy carbonyl, a cycloalkoxycarbonyl, an unsubstituted arylalkoxycarbonyl or a substituted arylalkoxycarbonyl, or $R^1$ and $R^2$ taken together form, with the nitrogen to which they are attached, a 5 to 7 membered ring, and $L^1$ and $L^2$ are, independently, a hydrocarbon linking group, a cycloalkyl, or an interphenylene.

4. The compound of claim 3 wherein

A is a group of the formula —$PO_3H$, or —$OSO_2OH$, or pharmaceutically acceptable salt thereof or physiologically hydrolyzable $(C_1–C_4)$alkyl or arylalkyl ester thereof;

$R^1$ is H, a linear or branched $(C_1$ to $C_6)$alkyl, a substituted or unsubstituted phenyl$(C_1–C_4)$alkyl, or a $(C_2–C_6)$ alkenyl;

$R_2$ is H, a linear or branched $(C_1$ to $C_6)$alkyl, a $(C_2–C_6)$ alkenyl, a substituted or unsubstituted phenyl $(C_1–C_4)$ alkyl, an acetyl, benzoyl or arylsulfonyl, a $(C_1–C_7)$ alkoxycarbonyl, —$OCOCH_2CH=CH_2$, a $(C_3–C_8)$ cyclo $(C_1–C_8)$ alkoxycarbonyl, —$OCOCH_2C_6H_5$ or a substituted arylalkoxycarbonyl wherein the substituent is a halogen, a nitro group, an amino group or a methoxyl group;

or $R^1$ and $R^2$ taken together form, with the nitrogen to which they are attached, a 5 to 7 membered ring; and $L^1$ and $L^2$ are, independently, a linear or branched chain alkyl of the formula —$(C_nH_{2n})$— wherein n is 1 to 8; a cycloalkyl of 3 to 8 carbon atoms, or an interphenylene.

5. A pharmaceutical composition comprising the compound according to one of claims 1 or 3 and a pharmaceutically acceptable carrier.

* * * * *

---

2. The compound of claim 1 wherein

A is a group of the formula —$PO_3H$, —$SO_3H$, —$OPO(OH)_2$, —$OSO_2OH$, or —SH, or pharmaceutically acceptable salt thereof or physiologically hydrolyzable $(C_1–C_4)$alkyl or arylalkyl ester thereof,

$R_1$ is H, a linear or branched $(C_1$ to $C_6)$alkyl, a substituted or unsubstituted phenyl$(C_1–C_4)$alkyl, or a $(C_2–C_6)$ alkenyl;

$R_2$ is H, a linear or branched $(C_1$ to $C_6)$alkyl, a $(C_2–C_6)$ alkenyl, a substituted or unsubstituted phenyl $(C_1–C_4)$ alkyl, an acetyl, benzoyl or arylsulfonyl, a $(C_1–C_7)$ alkoxycarbonyl, —$OCOCH_2CH=CH_2$, a $(C_3–C_8)$ cyclo$(C_1–C_8)$alkoxycarbonyl, —$OCOCH_2C_6H_5$ or a substituted arylalkoxycarbonyl wherein the substituent is a halogen, a nitro group, an amino group or a methoxyl group;

or $R^1$ and $R^2$ taken together form, with the nitrogen to which they are attached, a 5 to 7 membered ring; and $L_1$ and $L^2$ are, independently, a linear or branched chain alkyl of the formula —$(C_nH_{2n})$— wherein n is 1 to 8; a cycloalkyl of 3 to 8 carbon atoms, or an interphenylene, with the provisos that the compound of formula I is or